United States Patent [19]

Ooms et al.

[11] Patent Number: 5,679,825
[45] Date of Patent: Oct. 21, 1997

[54] PROCESS FOR THE PRODUCTION OF ARYL CARBONATES

[75] Inventors: Pieter Ooms; Hans-Josef Buysch, both of Krefeld, Germany

[73] Assignee: Bayer AG, Leverkusen, Germany

[21] Appl. No.: 583,882

[22] Filed: Jan. 11, 1996

[30] Foreign Application Priority Data

Jan. 18, 1995 [DE] Germany ............... 195 01 364.6

[51] Int. Cl.$^6$ .................................................. C07C 69/96
[52] U.S. Cl. ........................... 558/274; 558/260; 558/270
[58] Field of Search ........................... 558/260, 270, 558/274

[56] References Cited

U.S. PATENT DOCUMENTS

| | | | |
|---|---|---|---|
| 2,362,865 | 11/1944 | Tryon et al. | 260/463 |
| 2,837,555 | 6/1958 | Lee | 260/463 |
| 3,234,263 | 2/1966 | Kurkjy et al. | 260/463 |
| 5,239,105 | 8/1993 | Pews et al. | 558/274 |

FOREIGN PATENT DOCUMENTS

| | | |
|---|---|---|
| 0 516 355 | 12/1992 | European Pat. Off. . |
| WO 91/06526 | 5/1991 | WIPO . |

OTHER PUBLICATIONS

Kirk–Othmer, Encyclopedia of Chemical Technololgy, 3rd Edition, vol. 13, pp. 812–818 (1981).
Kirk–Othmer, Enc. of Chem. Tech., 3rd Edition, vol. 20, pp. 412–415 (1982).
Kirk–Othmer, Enc. of Chem. Tech., 3rd Edition, vol. 20, pp. 654–673 (1982).
Ullmann's Encyclopedia of Industrial Chem., 5th Edition, vol. A17, pp. 341–361 (1991).
Ullmann's Enc. of Ind. Chem., 5th Edition, vol. A17, pp. 426–433 (1991).
Kirk–Othmer, Enc. of Chem. Tech., 3rd Edition, vol. 21, pp. 162–181 (1983).
Kirk–Othmer, Enc. of Chem. Tech., 3rd Edition, vol. 22, pp. 658–679 (1983).
Kirk–Othmer, Enc. of Chem. Tech., 3rd Edition, vol. 22, pp. 355–358 (1983).
Ullmann's Enc. of Ind. Chem., 5th Edition, vol. A5, pp. 61–77 (1985).
Kirk–Othmer, Enc. of Chem. Tech., 3rd Edition, vol. 22, pp. 601–627 (1983).

*Primary Examiner*—Marianne M. Cintins
*Assistant Examiner*—Dwayne C. Jones
*Attorney, Agent, or Firm*—Connolly & Hutz

[57] ABSTRACT

Carbonates with aromatic ester groups may be produced by reacting aromatic monohydroxy compounds with phosgene or with chlorocarbonates of aromatic monohydroxy compounds, wherein a temperature in the range from 50° to 450° C. and a pressure in the range from 0.05 to 20 bar are used in the presence of hard materials with metal-like properties (ceramic precursors) as heterogeneous catalysts.

18 Claims, No Drawings

PROCESS FOR THE PRODUCTION OF ARYL CARBONATES

BACKGROUND OF THE INVENTION

1. Field of the Invention

This invention relates to a process for the production of carbonates with aromatic ester groups by reacting aromatic monohydroxy compounds with phosgene or chlorocarbonates of aromatic monohydroxy compounds with elimination of hydrogen chloride in the presence of hard materials with metal-like properties (ceramic precursors) as heterogeneous catalysts.

2. Description of the Related Art

Carbonates with aromatic ester groups are suitable for the production of polycarbonates using the melt transesterification process, for the production of phenyl urethanes or are precursors to active ingredients in the pharmaceuticals and plant protection sector.

It is known that aryl carbonates may be obtained by phase interface phosgenation (Schotten-Baumann reaction) of aromatic hydroxy compounds. In this reaction, using solvents and sodium hydroxide solution is disadvantageous as the aqueous alkaline solution may bring about partial hydrolysis of phosgene or chlorocarbonate. In any case, large quantities of common salt are obtained as a secondary product. Care must also be taken to ensure solvent recovery.

It has thus been proposed to perform condensation without using solvents in the presence of tetramethylammonium halides as catalysts (U.S. Pat. No. 2,837,555). The quantities of catalyst required in this case are thus relatively large. 5 to 7 wt. % of catalyst, relative to the quantity of phenol introduced, must generally be used in order to achieve economic reaction rates; the reaction temperatures of 180° C. to 215° C. entail a risk of decomposition of the thermolabile tetramethylammonium halides. The catalyst must furthermore subsequently be removed by washing with water, so making its recovery considerably more difficult. Moreover, much more than the stoichiometrically necessary quantity of phosgene is consumed.

According to another process (U.S. Pat. No. 3,234,263), diaryl carbonates are obtained by heating phenyl chlorocarbonates in the presence of large quantities of alkali (alkaline-earth) metal compounds with tertiary nitrogen bases as catalysts. However, this process has the disadvantage that elevated temperatures must be used and the catalysts as well as alkali (alkaline-earth) metal compounds must be partially dissolved in order to achieve reaction times which even approach economic viability. In this process, half the initially introduced phosgene is lost as $CO_2$. The chlorocarbonates must moreover be synthesised in a separate, upstream processing stage.

According to U.S. Pat. No. 2,362,865, diaryl carbonates are obtained by phosgenating aromatic hydroxy compounds in the presence of metallic titanium, iron, zinc and tin or in the form of the soluble salts thereof, in particular the chlorides and phenolates. Although very good yields are achieved, it is difficult to separate the catalysts from the products. In the case of distillation, even a certain degree of volatility of these compounds and also thermal decomposition caused by these compounds, resulting in contamination, quality reduction and losses in yield, must be expected.

It thus seems sensible to use heterogeneous, insoluble catalysts, which substantially facilitate working up of the reaction mixture. Proposals have also been made in this connection. Thus, according to the teaching of EP-A-516 355, aluminium trifluoride is in particular recommended, which is optionally applied onto supports such as aluminosilicates. However, the synthesis of aluminium trifluoride is very elaborate and costly due to handling of fluorine or hydrofluoric acid. WO 91/06526 also describes metal salts on porous supports as catalysts for the reactions according to the invention. As is clear from the experimental examples, completely continuous phosgenation of phenol on such catalysts is possible only in the gas phase, which is however associated with relatively high reaction temperatures and the risk of decomposition of the sensitive chloroformates. Obviously, phosgenation of phenol with these catalysts cannot be performed in the liquid phase as the hot, liquid phenol leaches out the active catalyst constituents.

SUMMARY OF THE INVENTION

The object of the invention was thus to provide more readily obtainable, effective heterogeneous catalysts for the production of diaryl carbonates.

It has now been found that compounds of the general formula (III), such as for example titanium carbonitride or zirconium boride, constitute excellent catalysts for the reaction of phosgene or chlorocarbonates with aromatic hydroxy compounds. This is particularly surprising and unexpected because, according to the prior teaching of WO 91/06526, oxides of metals such as titanium and zirconium are preferably stated as resistant and inert support materials.

DESCRIPTION OF THE PREFERRED EMBODIMENT

The present invention provides a process for the production of aryl carbonates by reacting aromatic monohydroxy compounds with phosgene or chlorocarbonates of aromatic monohydroxy compounds, characterised in that temperatures in the range from 50° to 450° C., optionally at a pressure of 0.05 to 20 bar, are used in the presence of compounds of the general formula (III)

$$A_xB_yC_zD_w \quad (III),$$

in which

A denotes an element from groups 3–10, 13 and 14 of the periodic system of the elements according to IUPAC-notation and B denotes an element from groups 13, 14, 15 and 16 and C denotes an element from groups 14 and 15 and D denotes an element from groups 14 and 15 and x denotes a number from 1 to 4 and y denotes a number from 1 to 4 and z denotes a number from 0 to 4 and w denotes a number from 0 to 4, as heterogeneous catalysts, wherein A, B, C and D each originate from different groups, but, in the case of an identical group, from different periods, providing that A is different from aluminium if B is carbon and simultaneously z and w are equal to 0.

The process according to the invention has the major advantage that the catalyst may be very easily separated and no contaminants remain in the crude reaction product. Working up is consequently substantially simplified.

Aromatic monohydroxy compounds for the process according to the invention are those of the formula $$Ar^1-OH \quad (I),$$

in which

Ar¹ means phenyl, naphthyl, anthryl, phenanthryl, indanyl, tetrahydronaphthyl or the residue of a 5- or 6-membered aromatic heterocycle with 1 or 2 heteroatoms from the group comprising N, O and S, wherein these isocyclic and heterocyclic residues may be substituted by 1 or 2 substituents such as linear or branched $C_1$–$C_4$ alkyl, linear or branched $C_1$–$C_4$ alkoxy, which may be substituted with phenyl, cyano and halogen (for example F, Cl, Br) and wherein the heterocyclic residues may moreover be combined with a fused benzene ring.

Examples of aromatic monohydroxy compounds of the formula (I) are: phenol, o-, m- and p-cresol, o-, m- and p-isopropylphenol, the corresponding halogeno- or alkoxyphenols, such as p-chlorophenol or p-methoxyphenol, as well as monohydroxy compounds of naphthalene, anthracene and phenanthrene and also 4-hydroxypyridine and hydroxyquinolines. Optionally substituted phenols are preferably used, very particularly preferably phenol itself.

The process according to the invention may be performed both with phosgene and with chlorocarbonates of aromatic monohydroxy compounds. In the event of performance with phosgene, the chlorocarbonate is initially produced, which is reacted to yield the diaryl carbonate with further aromatic monohydroxy compound present in the reaction mixture.

If chlorocarbonates and an aromatic monohydroxy compound are used as the starting materials, symmetrical or asymmetrical carbonates may be obtained.

Suitable aromatic chlorocarbonates for the process according to the invention are those of the formula (II)

$$Ar^1-OCOCl \qquad (II),$$

in which

Ar¹ has the meaning stated in formula (I).

Suitable catalysts for the purposes of the invention are compounds of the general formula (III)

$$A_xB_yC_zD_w \qquad (III),$$

in which

A denotes an element from groups 3–10, 13 and 14 of the periodic system of the elements according to IUPAC-notation and B denotes an element from groups 13, 14, 15 and 16 and C denotes an element from groups 14 and 15 and D denotes an element from groups 14 and 15 and x denotes a number from 1 to 4 and y denotes a number from 1 to 4 and z denotes a number from 0 to 4 and w denotes a number from 0 to 4.

The following may be cited as examples of A: Ti, Zr, Hf, V, Nb, Ta, Cr, Mo, W, Y, La, Al, Ga, In, Tl, Mn, Tc, Re, Fe, Co, Ni, Sn, Pb, Ge, Cu, Ag, Au and Zn, preferred elements are Ti, Zr, Hf, V, Nb, Ta, Cr, Mo, W, Y, La, Al, Si, Sn, Mn, Fe, Ni, Cu and Zn, particularly preferred elements are Ti, Zr, V, Nb, Ta, Mo, W, Al and Si.

The following may be cited as examples of B:

B, C, Si, N, P, Se and Te, preferred elements are B, C, Si, N, P and Te, particularly preferred elements are B, C, Si, N and P.

The following may be cited as examples of C: C and N.

The following may be cited as examples of D: C and N.

In the formula (III), one or more elements A, B, C or D may also occur adjacent to each other in different valencies.

The compounds of the formula (III) may be produced from different precursors, for example metal salts, metal oxides and metals.

These compounds and production process for such compounds are described, for example, in Kirk-Othmer, *Encyclopedia of Chemical Technology*, 3rd edition, volume 20, page 414 et seq., page 658, volume 21, page 169 et seq., volume 22, page 355 et seq., page 622 et seq., page 659 et seq., volume 13, page 814 et seq., New York 1969/1983, Ullmann's *Encyclopedia of industrial chemistry*, 5th edition, volume A5, page 61 et seq., volume 17, page 429 et seq., volume A17, page 341 et seq., Weinheim 1966/1991.

Hard materials with metal-like properties (ceramic precursors) are particularly suitable as heterogeneous catalysts.

They may be present in crystalline form in various modifications. They may be entirely or partially amorphous.

The catalysts which may be used in the process according to the invention are preferably carbides, nitrides, carbonitrides, borides, boron carbonitrides, phosphides, silicides and phosphorus nitrides, for example titanium carbide, titanium nitride, titanium carbonitride, titanium monoboride, titanium diboride, titanium silicides, such as titanium disilicides, zirconium carbide, zirconium nitride, zirconium carbonitride, zirconium diboride, zirconium silicide, zirconium phosphide, hafnium nitride, tungsten carbide, ditungsten carbide, tungsten nitride, ditungsten nitride, tungsten boride, ditungsten boride, ditungsten pentaboride, tungsten disilicides, ditungsten trisilicides, pentatungsten trisilicides, vanadium carbide, divanadium carbide, vanadium nitride, vanadium boride, vanadium diboride, vanadium silicide, divanadium silicide, vanadium phosphide, vanadium diphosphide, divanadium phosphide, trivanadium phosphide, vanadium selenide, vanadium telluride, vanadium arsenide, niobium carbide, niobium nitride, tantalum nitride, ditantalum nitride, tantalum carbide, tantalum boride, dimolybdenum nitride, lanthanum hexaboride, yttrium hexaboride, uranium nitride, thorium nitride, cerium nitride, chromium nitride, manganese nitride, tellurium nitride, rhenium nitride, iron nitride, cobalt nitride, nickel nitride, copper nitride, silver nitride, gold nitride, zinc nitride, cadmium nitride, mercury nitride, boron nitride, aluminium nitride, gallium nitride, indium nitride, tellurium nitride, silicon nitride, zinc nitride, germanium nitride, together with ternary substances, for example tantalum zirconium carbide, tantalum hafnium carbide, niobium tungsten carbides and quaternary substances, for example titanium boron carbonitride, titanium phosphorus carbonitride, zinc boron carbonitride.

For the purposes of the invention, the catalysts may be used dried, anhydrous, partially dried or undried.

Preferred catalysts have BET surface areas of 0.1 to 500 $m^2/g$, particularly preferably of 0.5 to 200 $m^2/g$ and very particularly preferably of 1 to 100 $m^2/g$. Acidic, neutral and basic catalysts may be used.

The catalysts may be used, for example, as powder or shaped articles and, after the reaction, may be removed, for example, by filtration, sedimentation or centrifugation. When arranged as a fixed bed, the catalysts are preferably used as shaped articles, for example as spheres, cylinders, rods, hollow cylinders, rings etc.

When used in suspended form, the catalysts are used in stirred vessels or bubble columns in quantities of 0.5 to 100 wt. %, preferably of 5 to 100 wt. % and particularly preferably of 5 to 50 wt. %, relative to the introduced quantity of monohydroxy compound.

In the event of continuous operation co-currently or counter-currently or as a trickle phase or in the gas phase on a fixed bed catalyst, catalyst loadings of 0.1 to 20 g of aromatic hydroxy compound per g of catalyst per hour are used, preferably of 0.2 to 10 g $-g^{-1}$ $-h^{-1}$ and particularly preferably of 0.2 to 5 g $-g^{-1}$ $-h^{-1}$.

Catalysts used in discontinuous testing may be repeatedly used for identical feedstocks without cleaning. If there is a change of feedstock, the catalysts are conveniently cleaned by extraction with inert solvents, as are stated below by way of example as reaction media, or with alcohols, such as methanol, ethanol, isopropanol or butanol, with esters or amides of acetic acid or by treatment with superheated steam or air.

In the event of continuous operation, the catalysts used may remain in the reactor for extended periods. Regeneration may optionally proceed by passing over superheated steam, optionally with the addition of subordinate quantities of air (approximately 0.1 to 20 wt. %, relative to the introduced quantity of steam) at 150° to 800° C. or by passing over diluent gases, such as nitrogen or carbon dioxide, containing 0.01 to 20 wt. % of oxygen, or carbon dioxide alone at 200 to 800° C. The preferred regeneration temperature is 150° to 700° C., particularly preferably 200° to 600° C.

The process according to the invention is performed at a temperature in the range from 50° to 450° C., preferably from 100° to 400° C., particularly preferably from 100° to 350° C. During performance of the process according to the invention, the temperature may be varied within the stated range, preferably increased.

The process according to the invention is performed at a pressure of 0.05 to 20 bar, preferably of 1 to 5 bar.

The process according to the invention may be performed with the additional action of solvents such as aliphatic and aromatic hydrocarbons, such as pentane, hexane, octane, benzene, isomeric xylenes, diethylbenzene, alkylnaphthalenes, biphenyl; halogenated hydrocarbons, such as dichloromethane, trichloroethylene etc.

The process according to the invention may be performed both in the gas phase and the liquid phase.

The process is preferably performed in the melt phase, for example by introducing phosgene or a chlorocarbonate of the formula (II) into a suspension of a catalyst in a melt of the aromatic monohydroxy compound of the formula (I) and, on completion of the reaction, separating the catalyst, for example by filtration or centrifugation.

The process is performed in the gas phase by vaporising phosgene and phenol and passing the mixture over a bed of a catalyst in lumps arranged in a tube.

Another preferred embodiment of the synthesis is perfusion of a melt of the aromatic monohydroxy compound of the formula (I) containing suspended catalyst with phosgene or phosgene/hydrogen chloride mixtures or with chlorocarbonates of the formula (II) in a continuously operating bubble column or series of bubble columns.

Another preferred method of performance is the co-current process in which aromatic hydroxy compounds of the formula (I) and phosgene or chlorocarbonates of the formula (II) are introduced co-currently, for example as a trickle phase, into the top of a catalyst packing arranged in a tube and hydrogen chloride and phosgenation products are discharged at the bottom of the tube.

Another preferred embodiment with particularly favourable results is the performance of the reaction according to the invention counter-currently in the trickle phase, wherein the aromatic monohydroxy compound of the formula (I) is introduced as a melt or as a solution into the top of a catalyst bed and a stream of phosgene or chlorocarbonate is fed from beneath countercurrently to this stream of liquid. This embodiment is conveniently performed in a vertical tubular reactor, which may also contain intermediate levels to improve the distribution of the gas and liquid stream.

Another preferred embodiment is the gas phase process at temperatures of 150° to 450° C., preferably of 180° to 350° C., at pressures of 0.05 to 2, preferably 0.1 to 0.8 bar.

In this process, pressure is varied relative to temperature in such a manner that the components remain in the gas phase and do not condense on the catalyst packing.

The molar ratio of the reaction partners aromatic monohydroxy compounds of the formula (I) to phosgene is 0.5 to 8:1, preferably 1.5 to 3:1. In this case, the equivalent molar ratio is 2:1.

The aromatic monohydroxy compound is correspondingly reacted with a chlorocarbonate in a molar ratio of 0.25 to 4:1, preferably of 0.8 to 1.5:1. In this case, the molar ratio is 1:1.

The crude aromatic carbonate obtained by heterogeneous catalysis is frequently already very pure and, once any residual hydrogen chloride or other volatile substances have been stripped out, may be used in this form for many purposes. For more demanding applications, the carbonate may optionally be further purified, for example by distillation or crystallisation.

EXAMPLES

H. C. Starck=H. C. Starck GmbH & Co. KG, Im Schleeke 78/91, D-38642 Goslar

Strem=Strem Chemicals, Inc. 7 Mulliken Way, Dexter Industrial Park Newburyport, Mass. 01950, U.S.A.

Example 1

0.42 mol/h of phosgene were continuously passed through 141 g (1.50 mol) of phenol in the presence of 14.1 g (10 wt. % relative to the phenol) of a powdered titanium carbide from H. C. Starck at 140° C. in a plane ground joint flask equipped with flow spoilers, a gas-dispersion stirrer and reflux condenser. After approximately 2 hours' reaction time, phenol conversion was 18.2%, wherein 0.04 g of phenyl chloroformate and 28.7 g of diphenyl carbonate were formed. Selectivity for carbonates was approximately 99%.

Example 2

Example 1 was repeated with 14.1 g of a powdered titanium nitride from H. C. Starck at 140° C. After 2 hours' reaction time, phenol conversion was 21.6%, wherein 0.03 g of phenyl chloroformate and 34.3 g of diphenyl carbonate were formed. Selectivity for carbonates was approximately 99%.

Example 3

Example 1 was repeated with 14.1 g of a powdered titanium carbonitride from H. C. Starck at 140° C. After 2 hours' reaction time, phenol conversion was 32.6%, wherein 52.1 g of diphenyl carbonate were formed. Selectivity was greater than 99%.

Example 4

Example 1 was repeated with 14.1 g of a powdered titanium diboride from H. C. Starck at 140° C. After 2 hours' reaction time, phenol conversion was 27.7%, wherein 0.06 g of phenyl chloroformate and 43.9 g of diphenyl carbonate were formed. Selectivity for carbonates was approximately 99%.

Example 5

Example 1 was repeated with 14.1 g of a titanium disilicide from Strem at 140° C. After 2 hours' reaction time, phenol conversion was 14.7%, wherein 23.4 g of diphenyl carbonate were formed. Selectivity was greater than 99%.

Example 6

Example 1 was repeated with 14.1 g of a powdered zirconium nitride from H. C. Starck at 140° C. After 2 hours' reaction time, phenol conversion was 9.4%, wherein 2.2 g of phenyl chloroformate and 12.5 g of diphenyl carbonate were formed. Selectivity for carbonates was 92.4%.

Example 7

Example 1 was repeated with 14.1 g of a powdered zirconium diboride from H. C. Starck at 140° C. After 2 hours' reaction time, phenol conversion was 35.7%, wherein 0.4 g of phenyl chloroformate and 54.9 g of diphenyl carbonate were formed. Selectivity for carbonates was greater than 96%.

Example 8

Example 1 was repeated with 14.1 g of a powdered aluminium nitride from H. C. Starck at 140° C. After 2 hours' reaction time, phenol conversion was 29.3%, wherein 46.4 g of diphenyl carbonate were formed. Selectivity was greater than 98%.

Example 9

Example 1 was repeated with 14.1 g of a powdered vanadium carbide from H. C. Starck at 140° C. After 2 hours' reaction time, phenol conversion was 16.3%, wherein 0.3 g of phenyl chloroformate and 25.5 g of diphenyl carbonate were formed. Selectivity for carbonates was 98.2%.

Example 10

Example 1 was repeated with 14.1 g of a powdered molybdenum disilicide from H. C. Starck at 140° C. After 2 hours' reaction time, phenol conversion was 8.7%, wherein 4.2 g of phenyl chloroformate and 10.3 g of diphenyl carbonate were formed. Selectivity for carbonates was approximately 95%.

Example 11

Example 1 was repeated with 14.1 g of a dimolybdenum carbide from H. C. Starck at 140° C. After 2 hours' reaction time, phenol conversion was 6.0%, wherein 5.1 g of phenyl chloroformate and 5.8 g of diphenyl carbonate were formed. Selectivity for carbonates was 97.3%.

Example 12

Example 1 was repeated with 14.1 g of a powdered tungsten monoboride from Strem at 140° C. After 2 hours' reaction time, phenol conversion was 17.3%, wherein 4.8 g of phenyl chloroformate and 24.2 g of diphenyl carbonate were formed. Selectivity for carbonates was approximately 99%.

Example 13

Example 1 was repeated with 14.1 g of a powdered ditungsten boride from Strem at 140° C. After 2 hours' reaction time, phenol conversion was 8.8%, wherein 4.7 g of phenyl chloroformate and 10.7 g of diphenyl carbonate were formed. Selectivity for carbonates was approximately 98%.

Example 14 (by way of comparison)

Example 1 was repeated without addition of catalyst at 140° C. After 2 hours' reaction time, phenol conversion was less than 0.2%.

Example 15

A mixture of 9.4 g (0.10 mol) of phenol and 15.7 g (0.10 mol) of phenyl chloroformate was heated to 100° C. in a three-necked flask fitted with a thermometer and reflux condenser in the presence of 0.94 g (10 wt. % relative to phenol) of a powdered titanium diboride from H. C. Starck. After 5 hours' reaction time, phenol conversion to diphenyl carbonate was found to be 68.6%. Carbonate selectivity was >99%.

Example 16

Example 15 was repeated with the same catalyst at 120° C. After 3 hours' reaction time, phenol conversion to diphenyl carbonate was 87.0%. Carbonate selectivity was >99%.

Example 17

Example 15 was repeated with the same catalyst at 140° C. After 1 hour's reaction time, phenol conversion to diphenyl carbonate was 76.5%. Carbonate selectivity was >99%.

Example 18

Example 15 was repeated with the same catalyst at 160° C. After 1 hour's reaction time, phenol conversion to diphenyl carbonate was 99%. Carbonate selectivity was >99%.

Example 19

Example 15 was repeated with 0.94 g of a powdered titanium carbide from H. C. Starck at 160° C. After 1 hour's reaction time, phenol conversion to diphenyl carbonate was 80.7%. Carbonate selectivity was >99%.

Example 20

Example 15 was repeated with 0.94 g of a titanium nitride from H. C. Starck at 160° C. After ½ hour's reaction time, phenol conversion to diphenyl carbonate was 80.0%. Carbonate selectivity was >99%.

Example 21

Example 15 was repeated with 0.94 g of a powdered titanium carbonitride from H. C. Starck at 160° C. After ½ hour's reaction time, phenol conversion to diphenyl carbonate was 94.1%. Carbonate selectivity was >99%.

Example 22

Example 15 was repeated with 0.94 g of a powdered zirconium diboride from H. C. Starck at 140° C. After 1 hour's reaction time, phenol conversion to diphenyl carbonate was 86.5%. Carbonate selectivity was >99%.

Example 23

Example 15 was repeated with 0.94 g of a powdered vanadium carbide from H. C. Starck at 160° C. After 1 hour's reaction time, phenol conversion to diphenyl carbonate was 84.4%. Carbonate selectivity was >99%.

Example 24

Example 15 was repeated with 0.94 g of a powdered tungsten monoboride from Strem at 160° C. After 5 hours' reaction time, phenol conversion to diphenyl carbonate was 74.4%. Carbonate selectivity was >99%.

We claim:

1. A process for the production of aryl carbonates by reacting aromatic monohydroxy compounds with phosgene or chlorocarbonates of aromatic monohydroxy compounds, wherein the reaction is performed at a temperature in the range from 50° to 450° C., at a pressure of 0.05 to 20 bar, in the presence of one or more compounds of the general formula (III)

$$A_xB_yC_zD_w \quad (III),$$

in which

A denotes an element selected from the group consisting of Y, La, Ti, Zr, Hf, V, Nb, Ta, Cr, Mo, W, Mn, Tc, Re, Fe, Co, Ni, Cu, Ag, Au, Zn, Al, Ga, In, Tl, Ge, Sn and Pb and B denotes an element selected from the group consisting of B, C, Si, N, P, Se and Te and C denotes an element selected from the group consisting of C and N and D denotes an element selected from the group consisting of C and N and x denotes a number from 1 to 4 and y denotes a number from 1 to 4 and z denotes a number from 0 to 4 and w denotes a number from 0 to 4, as heterogeneous catalysts, wherein A, B, C and D each originate from different groups of the periodic system of the elements, or, in the case of an identical group, from different periods, with the proviso that A is different from aluminum if B is carbon and simultaneously z and w are equal to 0.

2. Process according to claim 1, characterised in that the catalysts used are one or more compounds of the general formula (III) with surface areas measured using the BET method of 0.1 to 500 m²/g in quantities of 0.5 to 100 wt. % relative to the quantity of monohydroxy compound, in the event of incompletely continous operation, or with loadings of 0.1 to 20 grams of monohydroxy compound per gram of catalyst per hour in the event of completely continous operation.

3. The process of claim 1, wherein the reaction is performed at a temperature in the range from 100° to 400° C.

4. The process of claim 1, wherein the reaction is performed at a temperature in the range from 100° to 350° C.

5. The process of claim 1, wherein the reaction is performed at a pressure of 1 to 5 bar.

6. The process of claim 1, wherein a molar ratio of the aromatic monohydroxy compounds to the phosgene is 0.5 to 8.0:1.

7. The process of claim 1, wherein a molar ratio of the aromatic monohydroxy compounds to the phosgene is 1.5 to 3:1.

8. The process of claim 1, wherein a molar ratio of the aromatic monohydroxy compounds to the chlorocarbonates of aromatic monohydroxy compounds is 0.25 to 4:1.

9. The process of claim 1, wherein a molar ratio of the aromatic monohydroxy compounds to the chlorocarbonates of aromatic monohydroxy compounds is 0.8 to 1.5:1.

10. The process of claim 2, wherein the catalysts have a surface area measured using the BET method of 0.5 to 200 m²/g.

11. The process of claim 2, wherein the catalysts have a surface area measured using the BET method of 1 to 100 m²/g.

12. The process of claim 2, wherein the process is performed as an incompletely continuous operation and the catalysts are used in quantities of 5 to 100 wt. % relative to the quantity of monohydroxy compound.

13. The process of claim 2, wherein the process is performed as an incompletely continuous operation and the catalysts are used in quantities of 5 to 50 wt. % relative to the quantity of monohydroxy compound.

14. The process of claim 2, wherein the process is performed as a completely continuous operation and the catalysts are used at catalyst loadings of 0.2 to 10 grams of monohydroxy compound per gram of catalyst per hour.

15. The process of claim 2, wherein the process is performed as a completely continuous operation and the catalysts are used at catalyst loadings of 0.2 to 5 grams of monohydroxy compound per gram of catalyst per hour.

16. The process of claim 1, wherein the aromatic monohydroxy compounds have the following formula:

$$Ar^1\text{—}OH \quad (I),$$

in which

Ar¹ means phenyl, naphthyl, anthryl, phenanthryl, indanyl, tetrahydronaphthyl or the residue of a 5- or 6-membered aromatic heterocycle with 1 or 2 heteroatoms from the group comprising N, O and S, wherein these isocyclic and heterocyclic residues may be substituted by 1 or 2 substituents such as linear or branched $C_1$–$C_4$ alkyl, linear or branched $C_1$–$C_4$ alkoxy, which may be substituted with phenyl, cyano and halogen and wherein the heterocyclic residues may moreover be combined with a fused benzene ring.

17. The process of claim 1, wherein the aromatic monohydroxy compounds are selected from the group consisting of phenol, o- , m- or p- cresol, o-, m- or p-isopropylphenol, halogenophenols, alkoxyphenols, monohydroxy compounds of naphthalene, monohydroxy compounds of anthracene, monohydroxy compounds of phenanthrene, 4hydroxypyridene and hydroxyquinolines.

18. The process of claim 1, wherein the chlorocarbonates of aromatic monohydroxy compounds have the following formula:

$$Ar^1\text{—}OCOCl \quad (II),$$

in which

Ar¹ means phenyl, naphthyl, anthryl, phenanthryl, indanyl, tetrahydronaphthyl or the residue of a 5- or 6-membered aromatic heterocycle with 1 or 2 heteroatoms from the group comprising N, O and S, wherein these isocyclic and heterocyclic residues may be substituted by 1 or 2 substituents such as linear or branched $C_1$–$C_4$ alkyl, linear or branched $C_1$–$C_4$ alkoxy, which may be substituted with phenyl, cyano and halogen and wherein the heterocyclic residues may moreover be combined with a fused benzene ring.

* * * * *